US011365039B2

(12) United States Patent
Berga Ferres (10) Patent No.: US 11,365,039 B2
(45) Date of Patent: Jun. 21, 2022

(54) CARRYING DEVICE FOR BEVERAGE CANS

(71) Applicant: Josep Maria Berga Ferres, Sant Joan les Fonts (ES)

(72) Inventor: Josep Maria Berga Ferres, Sant Joan les Fonts (ES)

( * ) Notice: Subject to any disclaimer, the term of this patent is extended or adjusted under 35 U.S.C. 154(b) by 0 days.

(21) Appl. No.: 16/971,333

(22) PCT Filed: Feb. 19, 2019

(86) PCT No.: PCT/ES2019/070092
§ 371 (c)(1),
(2) Date: Aug. 20, 2020

(87) PCT Pub. No.: WO2019/162548
PCT Pub. Date: Aug. 29, 2019

(65) Prior Publication Data
US 2021/0086971 A1    Mar. 25, 2021

(30) Foreign Application Priority Data

Feb. 22, 2018   (ES) ............................. ES201830239U (51) Int. Cl.
*B65D 71/42*        (2006.01)

(52) U.S. Cl.
CPC ...... *B65D 71/42* (2013.01); *B65D 2571/0066* (2013.01); *B65D 2571/00259* (2013.01); *B65D 2571/00444* (2013.01)

(58) Field of Classification Search
CPC .......... B65D 71/42; B65D 2571/00259; B65D 2571/00444; B65D 2571/0066
USPC .................................................. 206/147–149
See application file for complete search history.

(56) References Cited

U.S. PATENT DOCUMENTS

| | | | |
|---|---|---|---|
| 2,936,070 A | | 5/1960 | Poupitch |
| 4,372,598 A | | 2/1983 | Quelch |
| 5,188,225 A | * | 2/1993 | Jorba ..................... B65D 71/46 206/145 |
| 5,551,566 A | * | 9/1996 | Sutherland ............. B65D 71/40 206/427 |
| 6,039,181 A | * | 3/2000 | Whiteside ............ B65D 71/125 206/427 |

(Continued)

FOREIGN PATENT DOCUMENTS

| | | |
|---|---|---|
| DE | 20319247 | 4/2004 |
| DE | 202018106535 | 1/2019 |
| WO | WO 2019/162548 | 8/2019 |

OTHER PUBLICATIONS

International Sarch Report and the Written Opinion dated Sep. 14, 2019 From the International Searching Authority Re. Application No. PCT/ES2019/070092. (12 Pages).

*Primary Examiner* — Rafael A Ortiz (57) ABSTRACT

The invention relates to a carrying device for beverage cans which allows the manual carrying of beverage cans grouped together in the form of a "pack", which device comprises a body devoid of side walls, having on its surface at least one opening defining a contour with proportions which allow the tight passage therethrough of a beverage can, the contour of said opening having a plurality of tabs that can be folded or bent in relation to the body itself and extending into the same opening, said tabs having a distribution according to at least one sequence, said sequence comprising two contiguous tabs followed by a gap followed by another tab followed by another gap.

11 Claims, 6 Drawing Sheets

(56) References Cited

U.S. PATENT DOCUMENTS

| | | | | |
|---|---|---|---|---|
| 6,293,392 B1 * | 9/2001 | Galbierz | ................ | B65D 71/40 |
| | | | | 206/148 |
| 6,394,272 B1 * | 5/2002 | Domansky | ........... | B65D 71/246 |
| | | | | 206/161 |
| 8,162,135 B2 * | 4/2012 | Oliveira | ................ | B65D 71/46 |
| | | | | 206/147 |

* cited by examiner

CARRYING DEVICE FOR BEVERAGE CANS

RELATED APPLICATIONS

This application is a National Phase of PCT Patent Application No. PCT/ES2019/070092 having International filing date of Feb. 19, 2019, which claims the benefit of priority of Spanish Patent Application No. U201830239 filed on Feb. 22, 2018. The contents of the above applications are all incorporated by reference as if fully set forth herein in their entirety.

FIELD AND BACKGROUND OF THE INVENTION

The object of the present invention application is the registration of a carrying device for beverage cans, which incorporates significant innovations and advantages over the techniques used up until now.

More specifically, the invention proposes the development of a carrying device for beverage cans which, because of its particular arrangement, allows the manual carrying of beverage cans grouped together in the form of a "pack", and in a manner that is more effective, safer and simpler for the user.

BACKGROUND OF THE INVENTION

The grouping together of beverage cans in the form of a "pack" for manual carrying thereof by the user is known in the current state of the art.

In this regard, patent application US2936070A discloses a receptacle for retaining a plurality of containers or the like having annular enlargements at one end in side-by-side substantially abutting and parallel relation, comprising a substantially unsupported sheet of plastic material. Said sheet of plastic material has a plurality of apertures therein and a plurality of fingers extending radially inwardly from the edge of each aperture which constitutes the root circle of the fingers. The apertures in the sheet are intended for association with the containers whereby such containers can be inserted through said apertures from a given direction when the material adjacent is stretched and deformed to form circumferentially continuous lips embracing said containers beneath said annular enlargements and resiliently gripping said containers with the fingers flexed upwardly for substantially their entire length from the root circle to lock beneath said annular enlargements and with the material of the fingers adapted to conform substantially to the adjacent external configuration of the containers associated therewith, and a handle associated with said sheet of plastic material for carrying said receptacle.

Nevertheless, said grouping together of beverage cans may present certain drawbacks, such as discomfort and difficulty in the manual carrying thereof, and it is particularly easy for the cans being carried to accidentally or unintentionally slip or fall out.

The present invention helps to solve and overcome the present problems as it allows the manual carrying of beverage cans grouped together in the form of a "pack", and in a manner that is more effective, safer and simpler for the user.

SUMMARY OF THE INVENTION

The present invention has been developed for the purpose of providing a carrying device for beverage cans, which is essentially characterised by the fact that it comprises a body devoid of side walls, having on its surface at least one opening defining a contour with proportions which allow the tight passage therethrough of a beverage can, the contour of said opening having a plurality of tabs that can be folded or bent in relation to the body itself and extending into the same opening, said tabs having a distribution according to at least one sequence, said sequence comprising two contiguous tabs followed by a gap followed by another tab followed by another gap.

Additionally, in the carrying device for beverage cans the sequence of the distribution of the tabs is repeated at least twice on the contour of the opening.

Alternatively, in the carrying device for beverage cans the sequence of the distribution of the tabs is repeated at least twice along the entire contour of the opening.

Preferably, in the carrying device for beverage cans the sequence of the distribution of the tabs is repeated four times along and occupying the entire contour of the opening.

Additionally, in the carrying device for beverage cans the tabs have a cut or incision in their region of contact with the contour of the openings.

Additionally, in the carrying device for beverage cans the body has added holes suitable for the passage of the user's fingers.

Preferably, in the carrying device for beverage cans the body is laminar.

Alternatively, in the carrying device for beverage cans the body has a rectangular geometry and six openings.

Additionally, in the carrying device for beverage cans the body has a symmetrical geometry.

Alternatively, in the carrying device for beverage cans the body incorporates an add-on having as many openings as openings of the body, said add-on being arranged such that it is collapsible or foldable over the body itself with each opening of the add-on coinciding with each opening of the body, the opening of the add-on furthermore having a width that is greater than the resulting width of the opening of the body with the added tabs and at the same time smaller than the width of the same opening of the body.

Additionally, in the carrying device for beverage cans the add-on is also laminar, the body and the add-on being arranged symmetrically with respect to one another.

As a result of the present invention, the manual carrying of beverage cans grouped together in the form of a "pack" in a manner that is more effective, safer and simpler for the user is achieved.

Other features and advantages of the carrying device for beverage cans will become apparent from the description of a preferred but not exclusive embodiment illustrated by way of non-limiting example in the attached drawings, in which:

DESCRIPTION OF SPECIFIC EMBODIMENTS OF THE INVENTION

Figure 1:
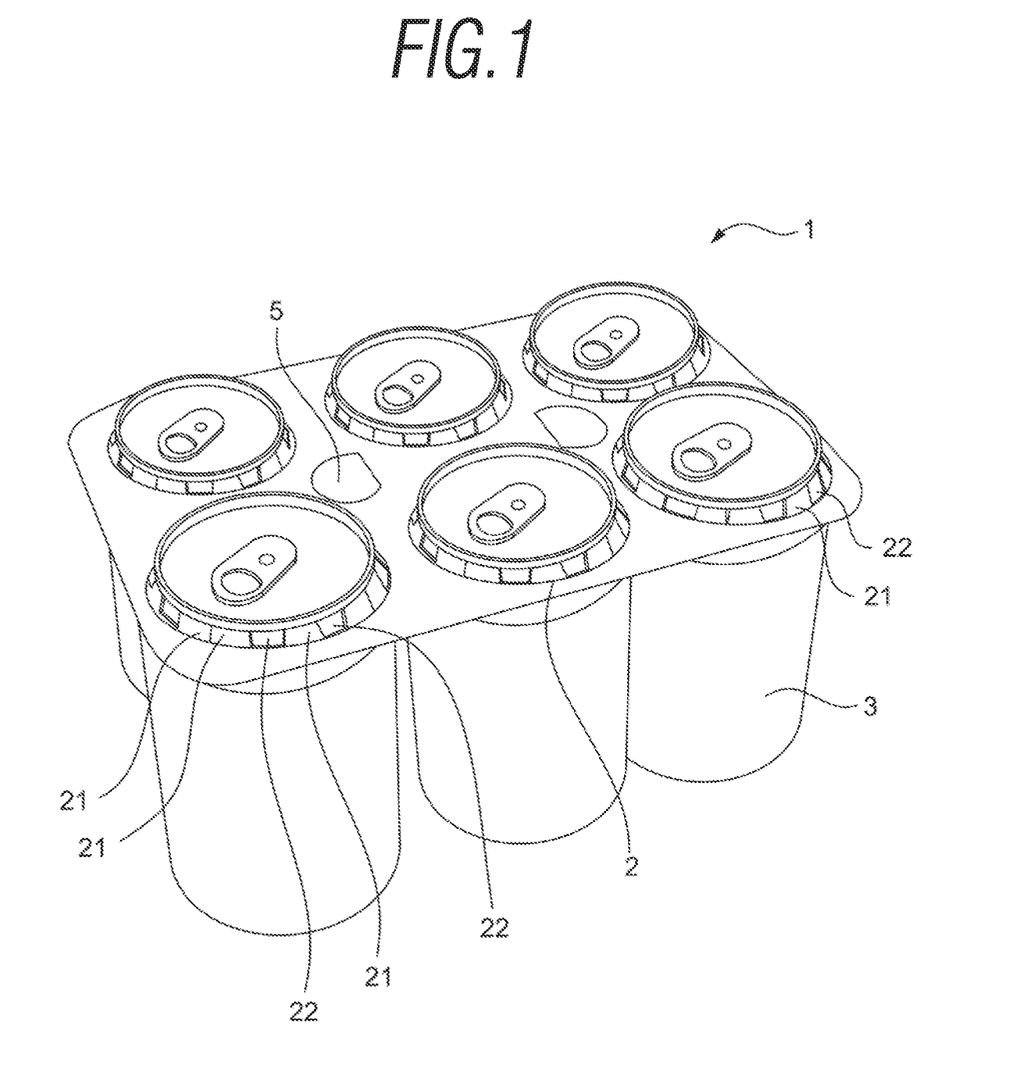
FIG. 1 is a schematic perspective view of a preferred embodiment of the carrying device for beverage cans of the present invention, in addition to being indicative of its use.
Figure 2:
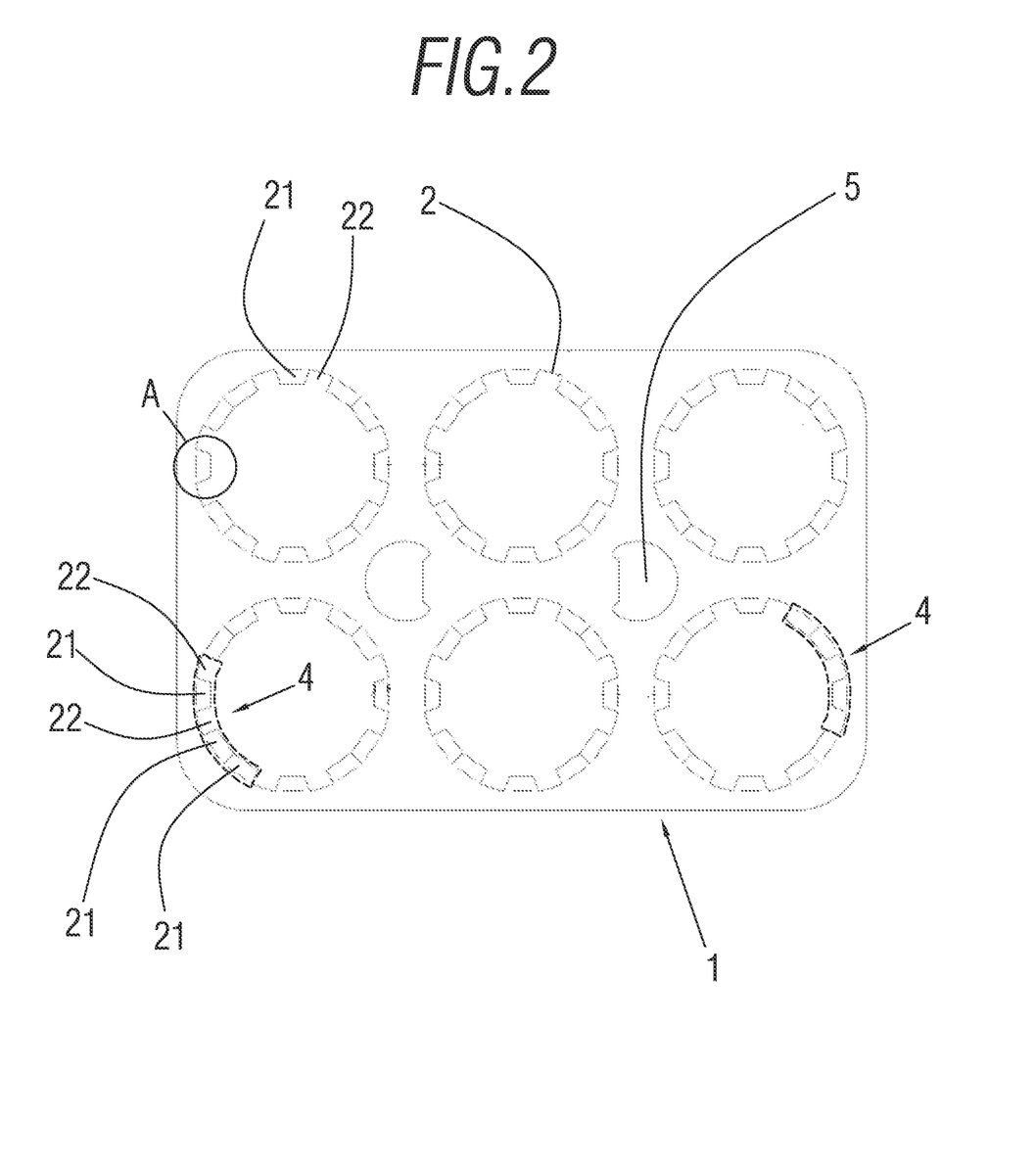
FIG. 2 is a schematic plan view of a preferred embodiment of the carrying device for beverage cans of the present invention.

As schematically shown in FIGS. 1 and 2, the carrying device for beverage cans comprises a body 1 devoid of side walls and having an exclusively planar dimension without extensions which are contained outside its own plane.

The body 1 has on its surface a plurality of openings 2 having a circular geometry and each of them defining an inner contour, with proportions which allow the tight passage therethrough of a beverage can 3, as can be seen in FIG. 1.

Furthermore, in the carrying device for beverage cans, the body 1 can be laminar, such as cardboard or the like, for example, and having a rectangular and symmetrical geometry and six openings 2, as depicted in FIG. 1, given that it is a useful arrangement during use.

Said openings 2 in turn have on their inner contour a plurality of radially distributed tabs 21 extending into the same openings 2, as can be seen particularly in FIG. 2, and being foldable or bendable in relation to the body 1 itself.

Specifically, in the carrying device for beverage cans, the tabs 21 have a distribution according to a sequence 4, said sequence 4 comprising two contiguous tabs 21 followed by a gap 22 followed by another tab 21 followed by another gap 22.

In the preferred embodiment schematically depicted in FIG. 2 and for better observation, the aforementioned sequence 4 of the distribution of the tabs 21 is marked by a discontinuous line and repeated four times along and occupying the entire contour of the opening 2.

This specific distribution with the sequence 4 of the tabs 21 and gaps 22 in the openings 2 schematically depicted in FIG. 2 is the most suitable for allowing the positioning of the beverage cans 3 inside the openings 2, and particularly and at the same time hindering them from unintentionally coming out, as can be seen in FIG. 1, which is an important improvement in relation to the known state of the art.

In that sense, the specific distribution and the described sequence 4 of the tabs 21 furthermore allows for a large surface of contact with the points for securing the cans 3, without it being complete at the same time, as that would hinder the removal of the cans 3 for consumption.

Furthermore, the tabs 21 have a cut 23 or incision in their region of contact with the contour of the openings 2. This is depicted more closely in the enlarged detail A of FIG. 3.

Figure 3:
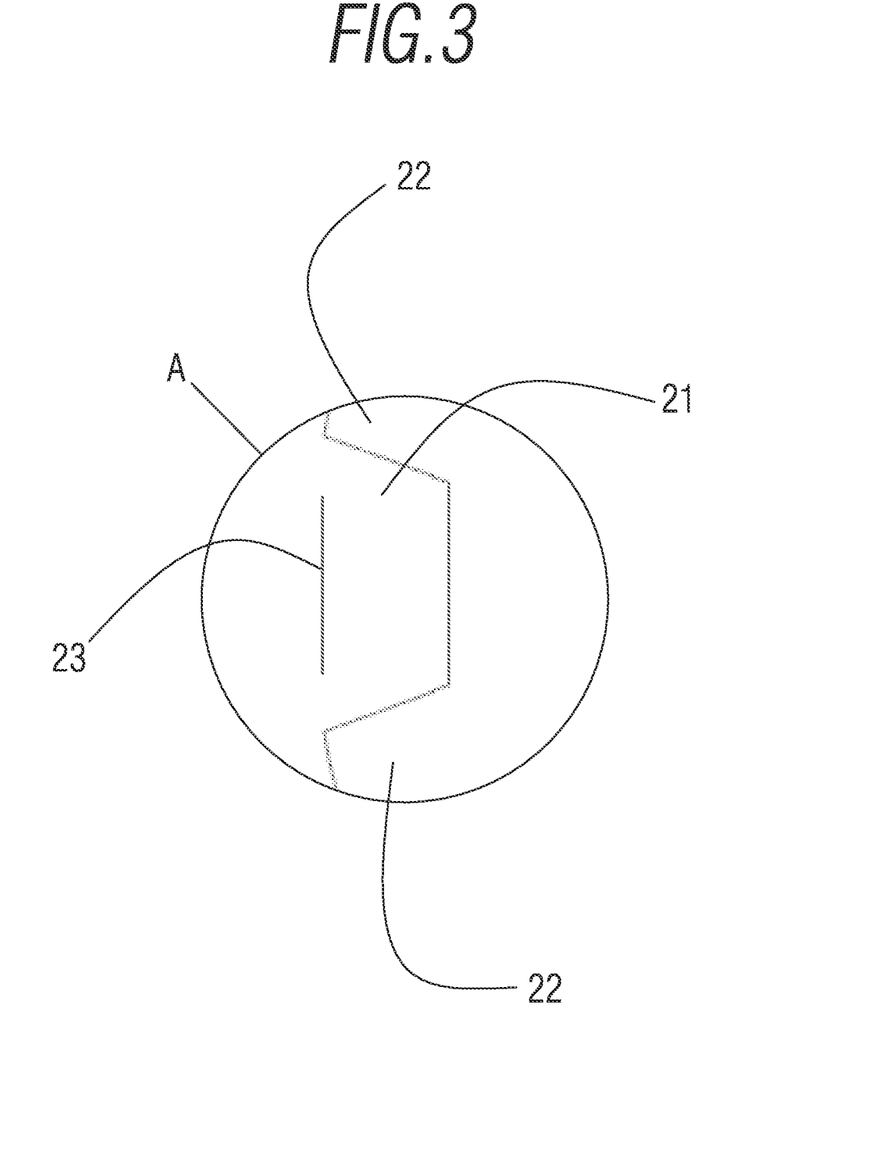
FIG. 3 is a schematic plan view of an enlarged detail of a preferred embodiment of the carrying device for beverage cans of the present invention.

The main function of the cut 23 is to facilitate and improve the use and performance of the carrying device for beverage cans of the present invention, as said cut 23 suitably weakens in the right proportion that region of contact of the tabs 21 with the contour of the openings 2. This means that when the cans 3 are introduced in said openings 2 by means of a piston during the manufacturing process, the latter has sufficient force to bend all the tabs 21 easily, and at the same time, the same tabs 21 put up resistance and secure the ring of the can 3 on its entire surface. This is also an important improvement in relation to the known state of the art.

The body 1 furthermore has added holes 5 suitable for the passage of the user's fingers, and thus allowing the manual carrying thereof.

Figure 4:
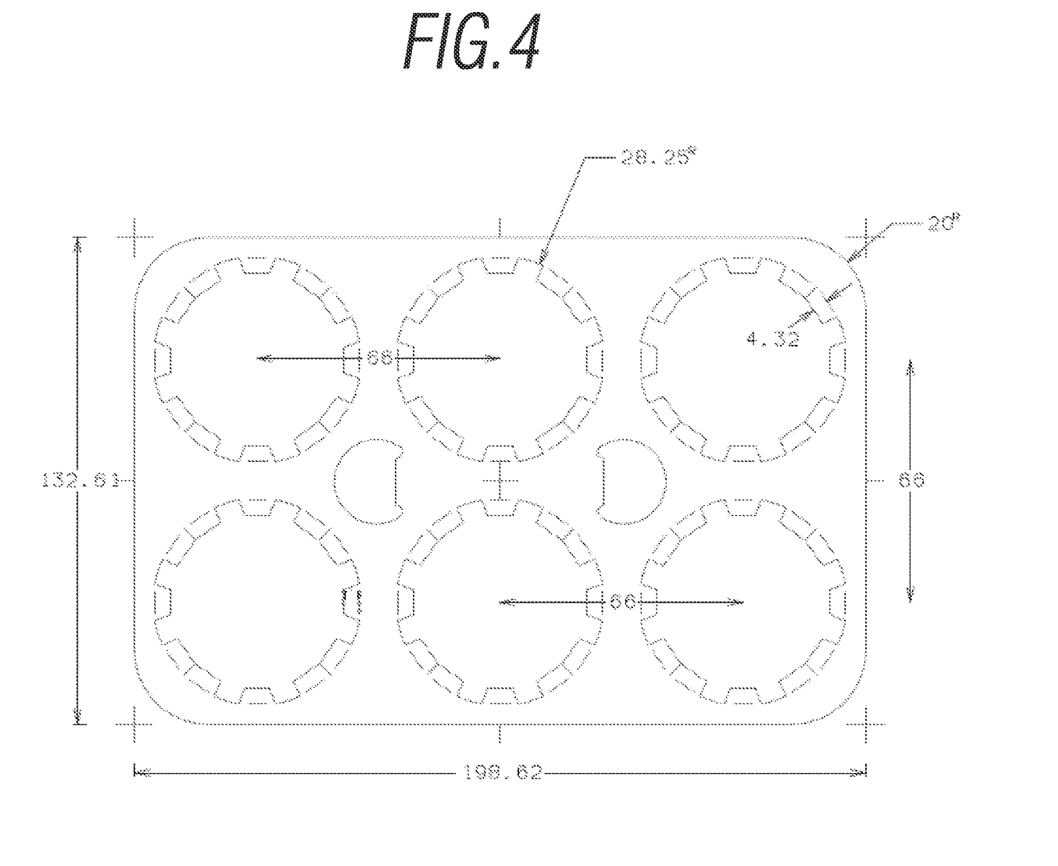
FIGS. 4 and 5 are schematic plan views of suitable geometric proportions of a preferred embodiment of the carrying device for beverage cans of the present invention.
Figure 5:
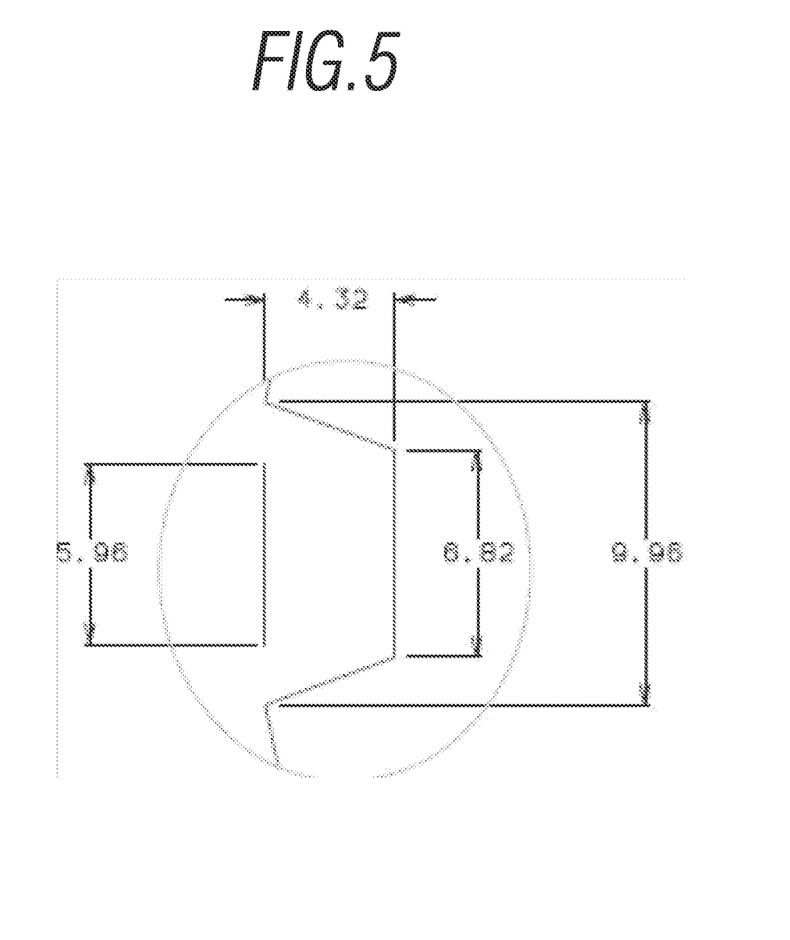

FIGS. 4 and 5 furthermore show suitable geometric proportions for the manufacture and use of the body 1 and tabs 21 and cut 23 or incision in a preferred embodiment of the carrying device for beverage cans of the present invention.

According to said preferred embodiment depicted in FIGS. 4 and 5 of the carrying device for beverage cans of the invention, the body 1 having a rectangular geometry has one side measuring 132.61 mm and another side measuring 198.62 mm, and the openings 2 have a radius of 28.25 mm, and the centres of the contiguous openings 2 between them have a separation of 66 mm. Also, the corners of the rectangular body 1 have a radius of 20 mm.

Likewise, according to said preferred embodiment of the carrying device for beverage cans of the invention, the tabs 21 have a trapezoidal geometry, with a major base measuring 9.96 mm and a minor base measuring 6.82 mm and a height of 4.32 mm, and the cut 23 or incision has a length of 5.96 mm.

Figure 6:
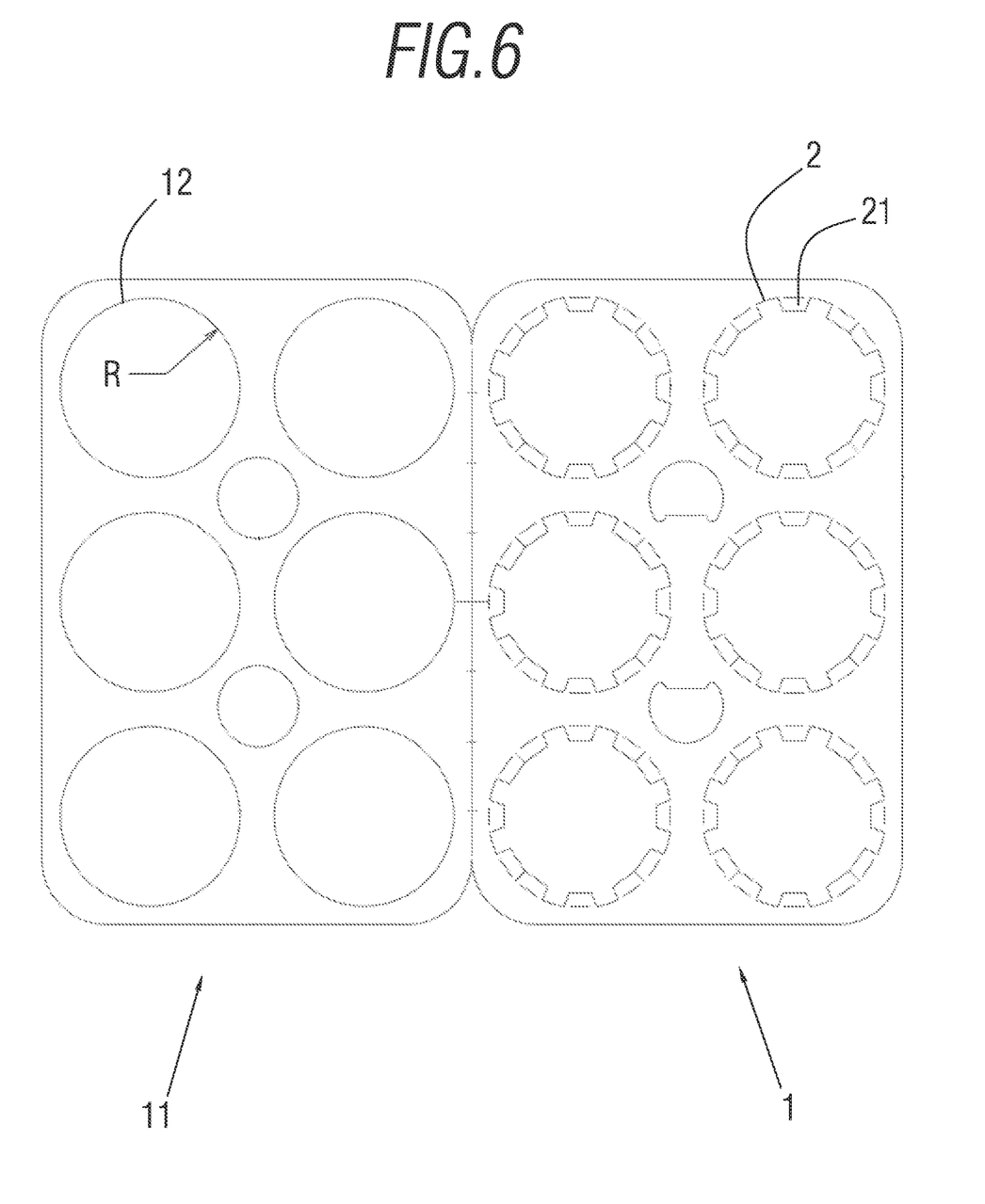
FIG. 6 is a schematic plan view of another preferred embodiment of the carrying device for beverage cans of the present invention.

In another preferred embodiment schematically depicted in FIG. 6, the body 1 incorporates an add-on 11 having openings 12, said add-on 11 being arranged such that it is collapsible or foldable over the body 1 itself with the openings 12 of the add-on 11 coinciding with the openings 2 of the body 1.

In the depiction of FIG. 6, the body 1 and the add-on 11 are laminar, have a rectangular geometry, and are arranged symmetrically with respect to one another, such that in the folding of the add-on 11 over the body 1, the openings 12 of the add-on 11 coincide with the openings 2 of the body 1.

Furthermore, the openings 12 of the add-on 11 have a width or radius R which is greater than the width or useful radius of the openings 2 of the body 1 taking into account the added tabs 21, and at the same time, the width or radius R of the openings 12 of the add-on 11 is less than the width or radius of the same openings 2 of the body 1.

In relation to the foregoing, width or useful radius of the opening 2 is understood to mean the width or radius of the opening 2 itself resulting from subtracting therefrom the height of the tab 21 having a trapezoidal geometry.

The width or radius R of the openings 12 of the add-on 11 in relation to the openings 2 of the body 1 thus prevent the tabs 21 from being able to bend inwardly.

With the arrangement described and depicted in FIG. 6, after the collapsing or folding of the add-on 11 over the body 1, since it has a laminar or double cardboard arrangement, the final useful and effective thickness increases, and therefore this alone improves the overall strength and securing during the use thereof.

According to the preceding explanation, the carrying device for beverage cans of the invention allows manual carrying by the user of beverage cans grouped together in the form of a "pack", in a manner that is more effective, safer and simpler than that known in the state of the art, furthermore exhibiting very good properties for the manufacture thereof.

The details, shapes, dimensions and other secondary elements, as well as the materials used in manufacturing the carrying device for beverage cans of the invention, may be suitably replaced with others that are technically equivalent and do not depart from the essential nature of the invention or from the scope defined by the claims included below.

What is claimed is:
1. A carrying device for beverage cans, comprising:
   a body (1) devoid of side walls, having on its surface at least one opening (2) defining a contour with proportions which allow the tight passage therethrough of a beverage can (3), wherein the contour of said opening (2) having a plurality of tabs (21) foldable or bendable in relation to the body (1) itself and extending into the same opening (2), wherein said tabs (21) having a distribution according to at least one sequence (4), said sequence (4) comprising two contiguous tabs (21) followed by a gap (22) followed by another tab (21) followed by another gap (22), wherein the body (1) incorporates an add-on (11) having as many openings (12) as openings (2) of the body (1), said add-on (11) being arranged such that it is collapsible or foldable over the body (1) itself with each opening (12) of the add-on (11) coinciding with each opening (2) of the body (1), the opening (12) of the add-on (11) furthermore having a width that is greater than the resulting width of the opening (2) of the body (1) with the added tabs (21) and at the same time smaller than the width of the same opening (2) of the body (1), wherein the width of the opening (12) of the add-on (11) being configured to prevent said tabs (21) from being able to bend towards an inner portion of the body (1) surrounding the opening (12).

2. The carrying device for beverage cans according to claim 1, wherein that the sequence (4) of the distribution of the tabs (21) is repeated at least twice on the contour of the opening (2).

3. The carrying device for beverage cans according to claim 1, wherein that the sequence (4) of the distribution of the tabs (21) is repeated at least twice along the entire contour of the opening (2).

4. The carrying device for beverage cans according to claim 1, wherein that the sequence (4) of the distribution of the tabs (21) is repeated four times along and occupying the entire contour of the opening (2).

5. The carrying device for beverage cans according to claim 1, wherein that the tabs (21) have a cut (23) or incision in their region of contact with the contour of the openings (2).

6. The carrying device for beverage cans according to claim 1, wherein that the body (1) has added holes (5) suitable for the passage of the user's fingers.

7. The carrying device for beverage cans according to claim 1, wherein that the body (1) is laminar.

8. The carrying device for beverage cans according to claim 1, wherein that the body (1) has a rectangular geometry and six openings (2).

9. The carrying device for beverage cans according to claim 1, wherein that the body (1) has a symmetrical geometry.

10. The carrying device for beverage cans according to claim 1, wherein the body (1) is laminar and the add-on (11) is also laminar, the body (1) and the add-on (11) being arranged symmetrically with respect to one another.

11. The carrying device for beverage cans according to claim 1, wherein the opening (2) of the body (1) and the opening (12) of the add-on (11) being circular, and wherein the opening (12) of the add-on (11) having a radius R that is greater than the resulting radius of the opening (2) of the body (1) with the added tabs (21) and at the same time smaller than the radius of the same opening (2) of the body (1).

* * * * *